United States Patent [19]
Williams et al.

[11] Patent Number: 5,814,281
[45] Date of Patent: Sep. 29, 1998

[54] RESISTIVE GAS SENSING

[75] Inventors: David Edward Williams, Abingdon; Ruth Ridley, London; Eliot Sizeland, Gorleston-on-Sea, all of Great Britain

[73] Assignee: Capteur Sensor & Analysers, Ltd., Didcot, United Kingdom

[21] Appl. No.: 732,271

[22] PCT Filed: May 1, 1995

[86] PCT No.: PCT/GB95/00986

§ 371 Date: Oct. 28, 1996

§ 102(e) Date: Oct. 28, 1996

[87] PCT Pub. No.: WO95/30143

PCT Pub. Date: Nov. 9, 1995

[30] Foreign Application Priority Data

Apr. 29, 1994 [GB] United Kingdom ................... 9408542

[51] Int. Cl.[6] .................................................. G01N 30/64
[52] U.S. Cl. .............................. 422/88; 422/90; 422/98; 422/83; 73/31.06; 73/23.2
[58] Field of Search ................... 422/88, 83, 90, 422/98; 73/31.06, 23.2

[56] References Cited

U.S. PATENT DOCUMENTS

| | | | |
|---|---|---|---|
| 4,147,515 | 4/1979 | Haas et al. | 23/232 E |
| 4,277,439 | 7/1981 | Yasuda et al. | 422/94 |
| 4,286,378 | 9/1981 | Micheli | 29/621 |
| 4,307,373 | 12/1981 | Johnston | 338/34 |
| 4,549,427 | 10/1985 | Kolesar, Jr. | 73/23 |
| 4,571,543 | 2/1986 | Raymond et al. | 422/88 X |
| 4,656,863 | 4/1987 | Takami et al. | 73/23 |
| 4,931,851 | 6/1990 | Sibbald et al. | 357/25 |
| 4,935,289 | 6/1990 | Kikuchi et al. | 428/209 |
| 4,948,680 | 8/1990 | Madou et al. | 429/13 |
| 5,143,696 | 9/1992 | Haas et al. | 422/90 |
| 5,185,130 | 2/1993 | Camanzi et al. | 422/90 |
| 5,296,196 | 3/1994 | Takeshima | 422/98 |
| 5,394,735 | 3/1995 | Fang et al. | 73/31.06 |
| 5,427,740 | 6/1995 | Coles et al. | 422/83 |
| 5,470,756 | 11/1995 | Coles et al. | 422/88 X |
| 5,478,528 | 12/1995 | Golunski et al. | 422/88 |
| 5,624,640 | 4/1997 | Potthast et al. | 422/90 |
| 5,635,136 | 6/1997 | Glaunsinger et al. | 422/88 |

*Primary Examiner*—Harold Y. Pyon
*Attorney, Agent, or Firm*—James B. Middleton

[57] ABSTRACT

A resistive gas sensor has a porous semiconducting oxide body in which the pore surfaces are decorated with a precious metal. The sensor operates at ambient temperatures for detection and measurement of target gases, especially carbon monoxide. The porous sensor body is formed of primary crystallites agglomerated together, the agglomerate size being less than 10 times the primary crystallite size, and the primary crystallite size having an average diameter of less than 5 micrometer. From 0.05 to 80% of the pore surfaces are covered by the metallic phase, the metallic phase consisting of particles having an average size of less than 50 nanometers. Presence of the target gas is indicated by a change in electrical resistance of the sensor.

19 Claims, 7 Drawing Sheets

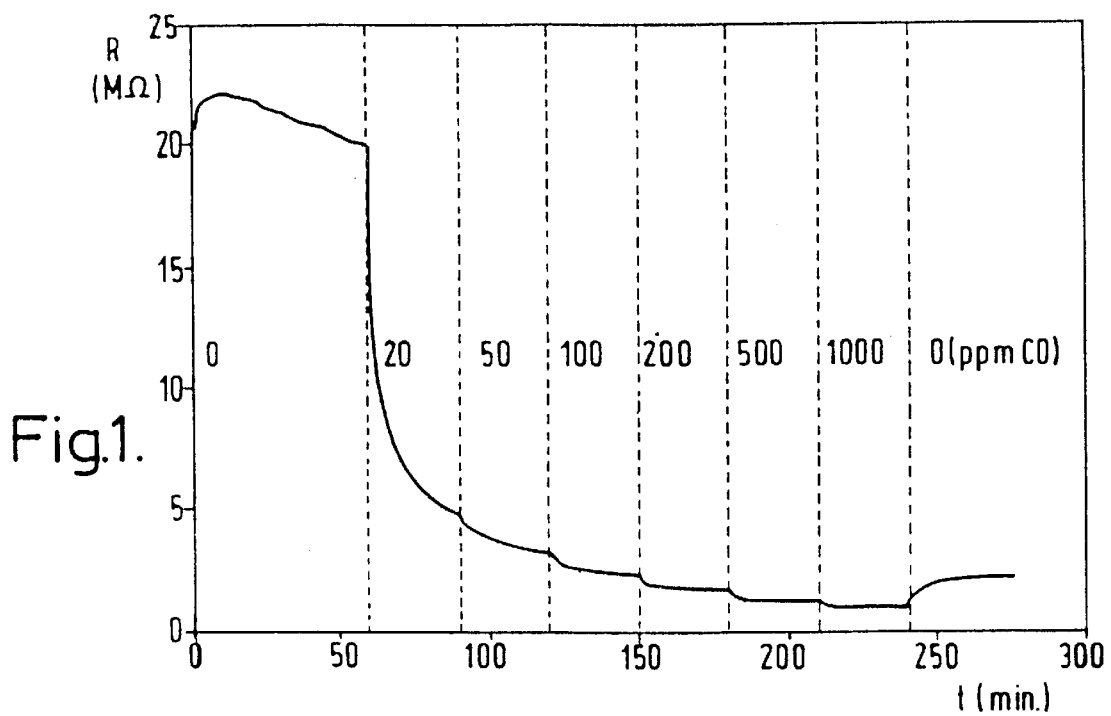
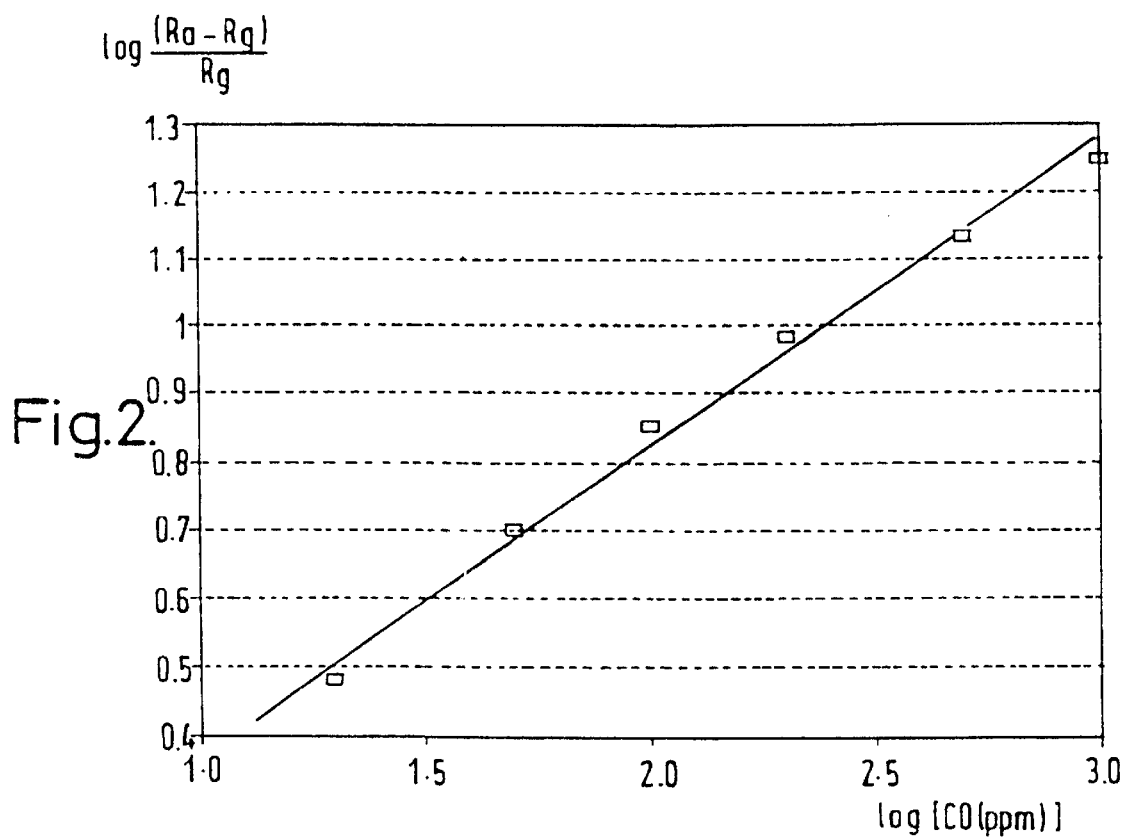

RESISTIVE GAS SENSING

This application is a 371 of PCT/GB95/00986 filed on May 1, 1995.

BACKGROUND OF THE INVENTION

1. Field of the Invention

This invention relates to the technical field of resistive gas sensing, that is to say methods of detecting or measuring a target gas in an atmosphere, and apparatus for use in performing such methods, and more particularly resistive gas sensors per se and methods of making such sensors.

2. Discussion of the Prior Art

A resistive gas sensor, or gas sensing resistor, generally comprises a body of porous semiconducting oxide carrying particles of a precious metal, such that the electrical resistance of the sensor varies on exposure to small concentrations of certain reactive gases in air.

It is known from prior art that a semiconducting oxide surface decorated with small amounts of metals such as platinum, palladium and silver show a variation of conductivity at ambient temperature (less than 100° C., and typically in the range 20 to 50° C.) on exposure to the above mentioned small concentrations of reactive gases in air. Examples of gases showing this effect are hydrogen, ammonia, ethene and carbon monoxide. Conjectures have been made that the effect depends on the presence of a sub-monolayer coverage of sufficiently small particles of the metal decorating the surface of the oxide, which is prepared in the form of a porous body. However, these conjectures have never been reduced to practice. The literature is silent on what an optimum composition might be, or how it might be achieved, and the previous work has not resulted in useful devices.

SUMMARY OF THE INVENTION

Five steps are involved in the preparation of such sensors:

1. Conditioning of the powder material from which the porous body is to be made. This includes, for example: the precipitation of the oxide or hydroxide from solution; control of the solution conditions; precipitation temperature; the rate at which reagent is added in order to control agglomerate size; and control of the concentration of solution additives, the purpose of which is to act as grain-growth inhibitors or promoters on the oxide (step 2 below), or to influence the nucleation and growth of the precious metal particles grown on the surface in steps 4 and 5 below.
2. Preparation of the semiconducting oxide, in the form of a porous artefact, by controlled calcination to obtain a desired specific surface area, porosity, and balance between macro-porosity and micro-porosity.
3. Impregnation of the porous body with a solution of a metal compound comprising a metal salt or complexion or organo-metallic complex colloidal dispersion. In particular, the impregnation time and temperature, the concentration of metal in the impregnating solution, and the nature and concentration of counter-ions and other cations present, require to be controlled.
4. Precipitation of a metal compound on to the oxide surface, either by:
   (a) controlled drying, or
   (b) exposure to the vapour of a water miscible organic solvent, in order to change the composition of the liquid within the pores, this being followed by drying, or
   (c) immersion in a water-miscible organic solvent, again followed by drying.
5. Decomposition of the metal compound so as to form the metal or oxide, for example by heating, with control of the heat-treatment time and temperature, and the gaseous atmosphere.

An object of the invention is to achieve reliable manufacture of ambient temperature gas sensors based on composites of a semiconducting oxide and one or more metals, particularly precious metals (e.g. Pt, Pd, Ir, Rh, Ag). The present document discloses particular characterisations which can be carried out to confirm that the desired microstructure has been obtained. If these characteristics are obtained, regardless of the details of the method of preparation, then a sensor having the required attributes of a reliable, ambient-temperature indication will be achieved. The invention is particularly directed at the detection of carbon monoxide at low concentrations (10 to 1000 ppm) in air at temperatures at or below 100° C., but this is without limitation as to either the identity of the target gas or the range of concentrations.

We have found that, in pursuit of the above object, the requirements for the choice of metal and semiconducting oxide can be framed very simply, in terms of: the energy of adsorption on the metal of the gas to be measured (the target gas); the electronic work function of the metal, both with adsorption from the air of oxygen only, and with adsorption of the gas to be detected; the work function and band gap of the oxide; and the electrical conductivity of the oxide.

More particularly:

1. The metal should be capable of adsorbing the target gas at room temperature. In general, this can involve displacement of adsorbed oxygen by the adsorbing gas. This adsorption should not be so strong as to be irreversible upon removal from the atmosphere of the gas to be detected from the atmosphere. On the other hand, it should not be so weak that it does not cause a detectable change in the work function of the metal surface.
2. The work function of the oxygen-covered metal should be less than that of the semiconducting oxide. More specifically, the electronic states associated with the oxygen-covered metal should lie within the band gap of the semiconducting oxide. The fact that this is so for any particular combination can be deduced from published tables and other literature, and can conveniently be confirmed by X-ray photo-electron spectroscopy.
3. The electrical conductivity of the semiconducting oxide should not be so low that measurements cannot conveniently be made. However, we have also found that the sensitivity is lost, and the response time becomes unacceptably long, if electrical conductivity is too high. In the case of composites of tin dioxide and platinum, it is known to increase electrical conductivity by doping the tin dioxide with antimony.
4. The microstructure of the material and the average surface energy of the structure of the sensor body should be such as to minimise the possibility of capillary condensation of water on to the surface.

Capillary condensation of water vapour occurs when the vapour pressure of water in the atmosphere exceeds that which would be in equilibrium with a droplet having a radius of curvature equal to the radius of the smallest pores in the microstructure. As the vapour pressure of water rises, progressively larger pores are filled. The effect of this waterlogging is to cover the active particles, so that access of gas to the active particles is denied. The result is a gradual degradation of the response.

We have found that, surprisingly, the above apparently very complex matrix of variables can be reduced to the control of just four quantities. These are as follows.

(a) The pore size distribution, primary crystallite size and agglomerate size of the oxide. Primary crystallite size and an estimate of pore size distribution are measurable by gas adsorption. Agglomerate size (agglomerates being clumps of primary crystallites), and pore size, are measurable by microscopic observation.

(b) The fraction of the oxide surface covered by the added metal.

(c) The size of the added metal crystallites (particles) decorating the surface.

(d) The average surface energy of the composite, as measured by the vapour pressure of water required to induce capillary condensation in a structure with pores in a given size range.

The paper by G. Sberveglieri et al, "A novel PVD technique for the preparation of $SnO_2$ thin films as $C_2H_5OH$ sensors", Sensors & Actuators, Vol. 7, Mar. 1992, pp 721–726, describes an experimental sensor for ethyl alcohol vapour in which the porous gas-sensitive material is a thin film of $SnO_2$ with an ultra-thin surface layer (0.1 nm) of palladium. High sensitivity to ethyl alcohol is obtained, but the working temperatures disclosed are above 300° C. and not ambient. Such a sensor is said to be highly selective to other alcohols and CO, and its non-sensitivity to CO is illustrated.

According to the invention in a first respect, a resistive gas sensor comprising a porous sensor body of a semiconducting oxide with a metallic phase decorating pore surfaces of the body, is characterized in that; the oxide has an agglomerate size less than 10 times its primary crystallite size, the latter being an average diameter of less than 5 micrometer; and in that a fraction of the pore surface area in the range 0.05–80% is covered by the metallic phase, the latter consisting of particles less than 50 nanometer in average size.

The oxide may be tin dioxide, and we have found that, to retain a good room-temperature sensitivity of the composite to carbon monoxide, its conductivity should not be greater than $2\times10^{-4}$ Siemen/cm.

The metallic phase preferably comprises at least one precious metal.

For the detection of carbon monoxide, the precious metals, particularly platinum and silver either alone or together or in conjunction with one or more of palladium, iridium or rhodium, have the required ability to adsorb carbon monoxide at room temperature.

The said fraction of the pore surfaces that is covered by the metallic phase is preferably in the range 1–30%. If this coverage is too low, then the response time becomes long, while at very low coverages, gas sensitivity disappears. By contrast, if the coverage is too high, then the metal provides an electrical short-circuit, the conductivity of the composite falls to a very low level, and gas sensitivity is lost.

The average particle size of the metallic phase is preferably less than 20 nanometer, and primary crystallite size is preferably less than 1 micrometer in average diameter.

Where the semiconducting oxide is tin dioxide, it may be doped with antimony. The latter is found to be segregated so as to be at its greatest concentration in the vicinity of the pore surfaces.

The sensor may include a room-temperature combustion catalyst, in particular for use in the sensing of carbon monoxide.

According to the invention in a second aspect, a method of making a resistive gas sensor is characterised by the steps of forming a porous sensor body by:

(1) making an intermediate material comprising a semiconducting oxide containing at least one metal compound; and (2) decomposing the metallic compound so as to deposit a metallic phase decorating pore surfaces of the body, step (1) being such as to give an agglomerate size of the oxide less than 10 times its primary crystallite size, and a primary crystallite size consisting of an average diameter of less than 5 micrometers, and steps (1) to (2) being such that the resulting metallic phase consists of particles less than 50 micrometers in average size, covering a fraction of the pore surface area in the range 0.5–80%.

The order of the steps 1 to 5 listed earlier herein may be varied. For example, the oxide powder can be exposed to a solution of the metal in a suitable form, then dried and formed into a suitable body before heat-treatment.

Alternatively, in accordance with a preferred feature of the invention, step (1) comprises making a mixture containing the said oxide and a metal compound, and capable of being applied to a substrate by printing; and printing the said mixture on to a substrate. The oxide powder may be mixed with a metal, either in the form of a salt, or as a solution of a salt, complexion or organo-metallic complex colloidal dispersion. It is then dried and formed into a paste, for example a paste suitable for screen-printing. This paste is deposited on a substrate and subjected to a heat treatment, which has the dual purpose of causing sintering and adhesion of the sensor material to the substrate, and of decomposing the metal salt to the metal.

The metal can also be deposited on the oxide from the vapour phase (for example in a controlled chemical vapour deposition), or deposited directly by a process such as sputtering or vacuum evaporation.

Many of these procedures are well known in the art for the manufacture of gas-sensitive resistors based on semiconducting oxides, particularly tin dioxide, intended for use at elevated temperatures (well above, say 120° C., and typically around 300° C.), to which end these sensors are provided with an appropriate heating element, the working temperature of which may, optionally, be carefully controlled.

According to some literature (J. F. McAleer et al, J Chem Soc Faraday Trans I, 84 (1988) p 441), such sensors might be expected to show a useful response at ambient temperature. However, we are not aware of any examples of any such sensor actually being operated commercially at ambient temperature, despite the advantages that such operation would confer in respect of the power consumption of the sensor and the consequent widening of its usefulness in portable apparatus or in domestic safety monitoring apparatus.

We have found that, if sensors containing precious metals are subjected to the known technique of applying heat treatment at temperatures sufficiently high to cause so-called "doping" of the semiconducting oxide, then the attributes of an ambient-temperature sensitivity to gases will be lost. We find that this loss of sensitivity occurs when the heat treatment temperature is, for example 800° C. or above, but not when it is as low as 600° C.

According to the invention in a third aspect, a method of detecting or measuring the concentration of a target gas in an atmosphere, at a temperature of 100° C. or less, is performed using a sensor according to the said first aspect, or a sensor made by the method of the said second aspect, of the invention.

The sensor may operate at the prevailing ambient temperature, application of heat to the sensor being absent. Alternatively, some heat may be applied to the sensor to raise its temperature of operation to a constant value just high enough to eliminate any effects of variation in ambient temperature on the sensor resistance.

The method may include momentary heating of the sensor once or intermittently, to a temperature and for a period of just sufficient magnitude to allow any condensed moisture present at the sensor to dissipate, the sensor being at the prevailing ambient temperature, or some constant temperature slightly above ambient, for the major part of its operation.

Although the resistance of a sensor made in accordance with the invention can easily be measured by conventional direct current (d.c.) methods, we have found that a much faster response time can be obtained, as well as a more stable baseline, if a pulsed d.c. measurement, or an alternating current (a.c.) measurement is used. By a pulsed d.c. measurement is meant one in which the potential difference across the sensor is maintained at zero for most of the time. When a measurement is to be made, a suitable potential difference is momentarily applied across the specimen, and the resistance is measured as quickly as possible before the potential difference is returned to zero.

We have found that an a.c. measurement can conveniently be made by connecting the sensor as part of the feedback network in an oscillator controlled by a resistance-capacitance network, one element of which is the sensor. The oscillator frequency then becomes inversely proportional to the sensor resistance.

According to the invention in a fourth aspect, apparatus for performing the method of the said third aspect of the invention is characterised by an oscillator circuit having a feedback network, for controlling the oscillator frequency and being a resistive-capacitive network, the sensor being one element of the latter.

The parameters listed as (a) to (d) earlier herein may be determined in the following way. The total surface area of the oxide is measured, for example, by the BET method involving adsorption of nitrogen or krypton gas at liquid nitrogen temperature. The loading of metal is determined, for example, by measurement of the increase in weight of the porous ceramic body following impregnation and decomposition of the metal compound.

The surface area of added metal exposed to the gas is determined, for example, by measurement of adsorption of carbon monoxide or hydrogen at room temperature. The apparent particle size of the oxide, and pore size distribution, are determined by examination under a scanning electron microscope. The composite is examined by X-ray photoelectron spectroscopy, with particular attention being paid to the regions of the spectrum corresponding to the valence band edge of the oxide and the core levels of the added metal. In general, such examination will show that the added metal appears to be in a variety of states, not necessarily best represented as free metal, but often better represented as metal oxide or hydroxide. Such examination should also show that the effect of the additive has been to introduce electronic states lying just above the valence band edge of the matrix oxide. An approximate estimate of surface energy with respect to the adsorption of water vapour can be made by examining the wetting of the material by a drop of water.

Calculation of average primary crystallite size (i.e. the crystallite size of the oxide): if S denotes the specific surface area of the oxide, as determined, for example, by the BET method using nitrogen adsorption; and if $\rho$ denotes the crystal density of the oxide, then the average effective crystallite radius, $<r_{cryst}>$ can be calculated from the formula $<r_{cryst}>=3/(S\rho)$. For the purpose of this calculation, the particles are assumed to be spherical.

Calculation of average metal crystallite size: if $S_{met}$ denotes the specific area of added metal (crystal density $\rho_{met}$) expressed per unit mass of the composite material (determined, for example, by adsorption of a reactive gas, which chemisorbs strongly on to the added metal but which shows negligible physisorption on to the oxide at room temperature); and if $W_{met}$ denotes the mass of added metal deposited per unit mass of composite, then the average added metal crystallite size $<r_{met}>$ can be expressed as $<r_{met}>=3W_{met}/\rho_{met}S_{met})$. For the purpose of this calculation, the particles are assumed to be hemispherical.

The fractional coverage of added metal can be expressed as $S_{met}/S$. Apparent fractional coverage can also be derived, based on the assumption that the added metal is deposited in the form of an atomic monolayer, and is convenient for the calculation of the amounts of metal to be added. An example of such a calculation is given in the examples later herein. The actual fractional coverage obtained in the fabricated sensor depends on the uniformity with which the metal is applied, and on the heat-treatment temperature.

Some further preferred features of the invention are as follows:

Where the sensor body is substantially hydrophobic and comprises the oxide mixed with a hydrophobic ceramic material, the ceramic may be silicallite.

The room-temperature combustion catalyst may be, for example, an alloy of platinum and iridium.

In the method according to the second aspect of the invention, step (1) preferably comprises: making a porous sensor body formed of the oxide; impregnating the sensor body with a solution containing at least one metal compound; and, precipitating the compound or compounds.

Step (1) may include mixing a hydrophobic ceramic material with the oxide to form a composite, and firing the composite onto a substantially hydrophobic surface of a support element. The method may then include the further step of dispersing a room-temperature combustion catalyst on the substantially hydrophobic surface of the said support element, whereby the sensor body comprises a three-phase composite.

The method may further include the step of drying the sensor and then treating its surface with a solution of a hydrophobic compound, such as chlorotrimethylsilane in hexane, and/or the step of doping the oxide with antimony in step (1).

In the method of using the sensor according to the third aspect of the invention, a zero potential is preferably applied across the sensor for a major part of its operation, with direct-current pulses being applied to the sensor whereby its resistance output signals are in the form of pulses.

In use, the sensor being preferably connected in a feedback network of an oscillator, the method of using the sensor preferably includes varying the oscillator frequency in response to changes in the resistance of the sensor, so that the output signals representing target gas concentrations are frequency signals.

BRIEF DESCRIPTION OF THE DRAWINGS

The invention will now be discussed in greater detail, and non-limiting examples of embodiments of the invention will be given. In this connection, reference will be made to the accompanying drawings, in which:

FIG. 1 is a diagram showing a typical resistance response for a resistive gas sensor, i.e. for a pellet constituting the body of the sensor, in one embodiment of the invention, when exposed to carbon monoxide in air at ambient temperature;

FIG. 2 is a graph in which the response in FIG. 1 is expressed logarithmically;

DETAILED DESCRIPTION OF THE EMBODIMENTS

Figure 3:
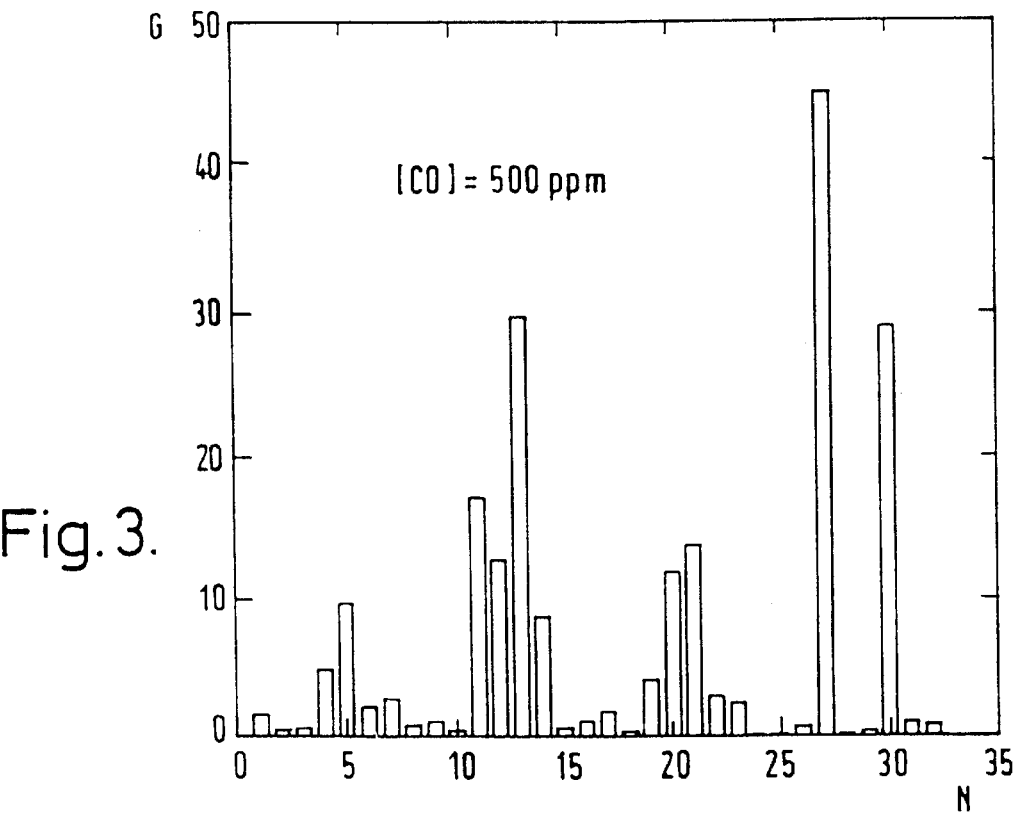
FIGS. 3 and 4, which are associated with the Tables given at the end of this Description, are diagrams illustrating the effect of platinum loading on the sensitivity, of a sensor in accordance with the invention, to carbon monoxide in two different concentrations at ambient temperature.

Example 1
Effect of platinum crystallite size and surface loading

Metastannic acid of commercial grade was calcined and pressed into pellets, 13 mm in diameter and 2 mm thick. The pore volume of the pellets was determined by weighing them first dry and then wet, after immersion in water such that the pore space was completely filled with water. The pore volume thereby determined was 0.15 cm$^3$ (corresponding to an apparent porosity of 56%). The surface area of the dry pellets was determined, by adsorption of krypton at liquid nitrogen temperature using the BET method, to be 3 m$^2$/g, giving an apparent primary crystallite size of approximately 0.1 micrometer. The agglomerate size was determined by scanning electron microscopy to be 0.4 to 2 micrometer. Platinum was deposited on to the surface of the tin dioxide, by impregnating the pellets with a solution of a platinum complex, following by drying and firing in air. The coverage of platinum was varied by variation of the concentration of the impregnating solution, using the following formula, in which $S_i$ denotes the platinum loading, i.e. the ideally required coverage of the surface by platinum, expressed as a percentage of a monolayer and assuming a hexagonal close-packed array of platinum atoms on the surface. The other quantities are: c, the concentration of the impregnation solution; $V_p$, the pore volume of the tin dioxide pellet; S, the surface area of tin dioxide; $r_o$, one half of the interatomic distance in platinum metal at room temperature; L, Avagadro's number.

$$c = \frac{7 S_i \cdot S}{900 L \pi r_0^2 V_p}$$

Great care was required to ensure uniform impregnation of the pellet. Uniform impregnation was not necessary in order to achieve a gas response, since a gas response would generally be obtained from that part of the pellet which was impregnated. However, uniform impregnation was desirable in order to avoid a large interference from the effects of varying relative humidity of the atmosphere. The impregnated pellets were fired in air at temperatures in the range 300° to 800° C. The surface area of platinum was obtained by measurement of the adsorption of carbon monoxide at room temperature (25° C.), and the state of the platinum on the surface was investigated by X-ray photo-electron spectroscopy. The variation of resistance with carbon monoxide concentration in the air was measured.

A typical resistance response for this sensor is shown in FIG. 1, to which reference is now made. FIG. 1 shows the resistance R of the pellet plotted against time when the pellet was exposed to a succession of known concentrations of carbon monoxide in a mixture of 21% oxygen and 79% argon. These concentrations are indicated on the appropriate vertical bands in the FIGURE, in parts per million (ppm) of CO, going from 0 to 1000 ppm and back to 0.

This response may be expressed as a power law:

$$(R_a-R_g)/R_g = K \cdot [CO]^\beta,$$

where $R_a$ and $R_g$ are the resistances in air and the target gas (in this case CO) respectively, and CO is the concentration of CO. This is illustrated in FIG. 2, which is a double logarithmic plot of $(R_a-R_g)/R_g$ against [CO]. The results of changes in the temperature for decomposition of the platinum salt, and in the loading of platinum, can conveniently be expressed in terms of the changes caused to the parameters k (gas sensitivity) and β (the exponent). High sensitivity is obtained at high values of both k and β.

Figure 4:
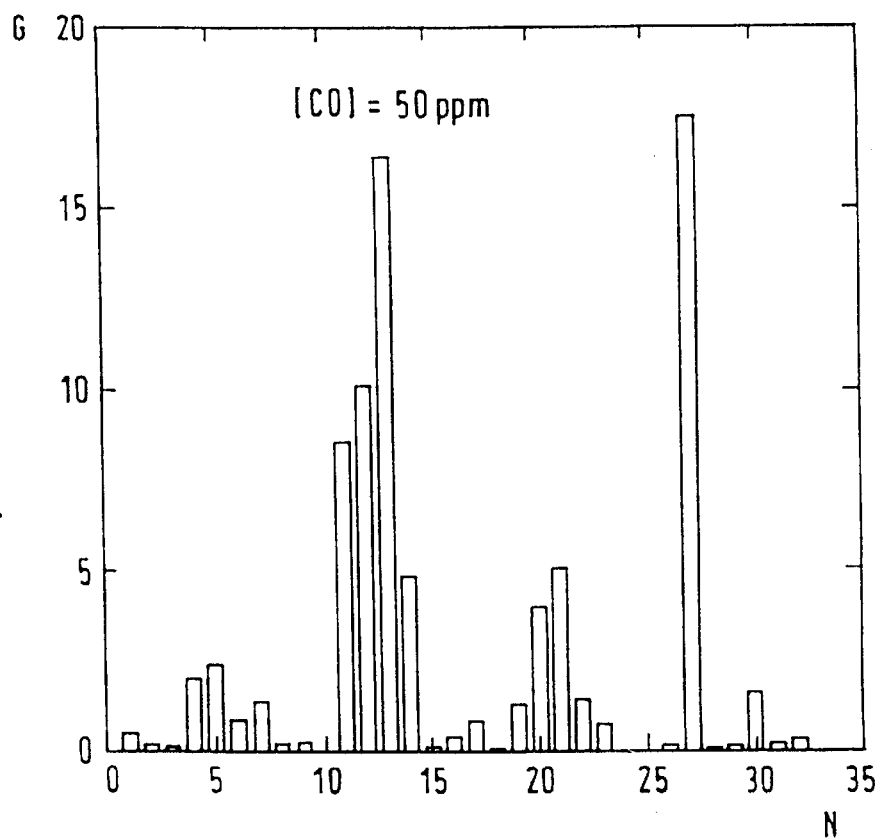

Reference is now made to FIGS. 3 and 4, each of which shows the response G, where G $=(R_a-R_g)/R_g$, for different, discrete, values of platinum loading $S_i$ and firing (decomposition) temperature T. In FIG. 3, the results were obtained in a concentration of CO of 500 ppm, while the CO concentration in FIG. 4 was 50 ppm. Each result is represented by a "line number" N, and the values of $S_i$ and T to which each line number corresponds are given at the end of this Description in Table 1 (for FIG. 3) and Table 2 (for FIG. 4).

In each of the tables, the first column is the line number N in the corresponding FIG. 3 or 4; the second column is platinum loading $S_i$, expressed here as the apparent fractional coverage calculated from the amount of platinum added, again as a percentage; and the third column is the firing temperature T in °C..

FIGS. 3 and 4 indicate that the sensitivity decreases, by and large, with decreasing platinum loading. A response can be obtained with surprisingly small platinum loading ($S_i$ as low as 0.025%). Optimum results were obtained with $S_i$ in the range 1 to 50%.

Figure 5:
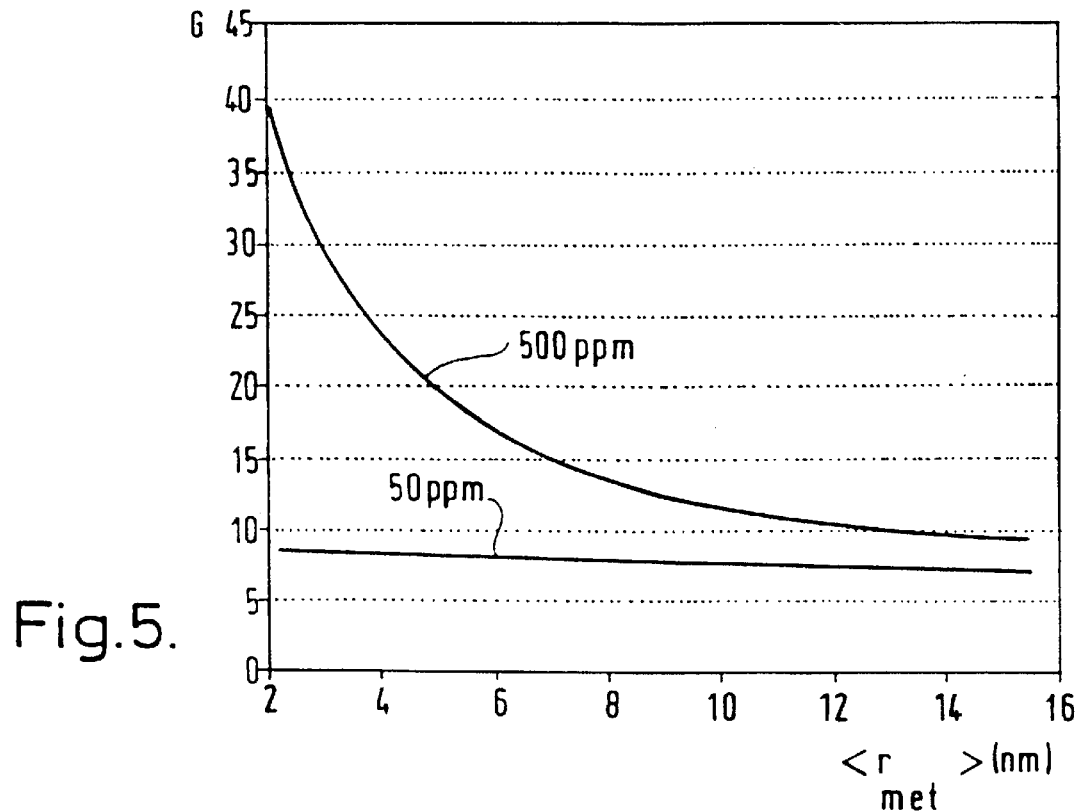
FIG. 5 is a diagram showing the effect of average apparent crystallite size on the response of the same sensor under the same conditions.

Although FIGS. 3 and 4 show some systematic trends, there is also much scatter in the data, particularly with respect to the effect of the firing temperature. In this connection, reference is now made to FIG. 5, which shows that the magnitude of the response G (defined above), and therefore the sensitivity of the sensor, varies systematically with the apparent average crystallite size $<r_{met}>$. The effect of increasing firing temperature is generally to increase the value of $<r_{met}>$.

Figure 6:
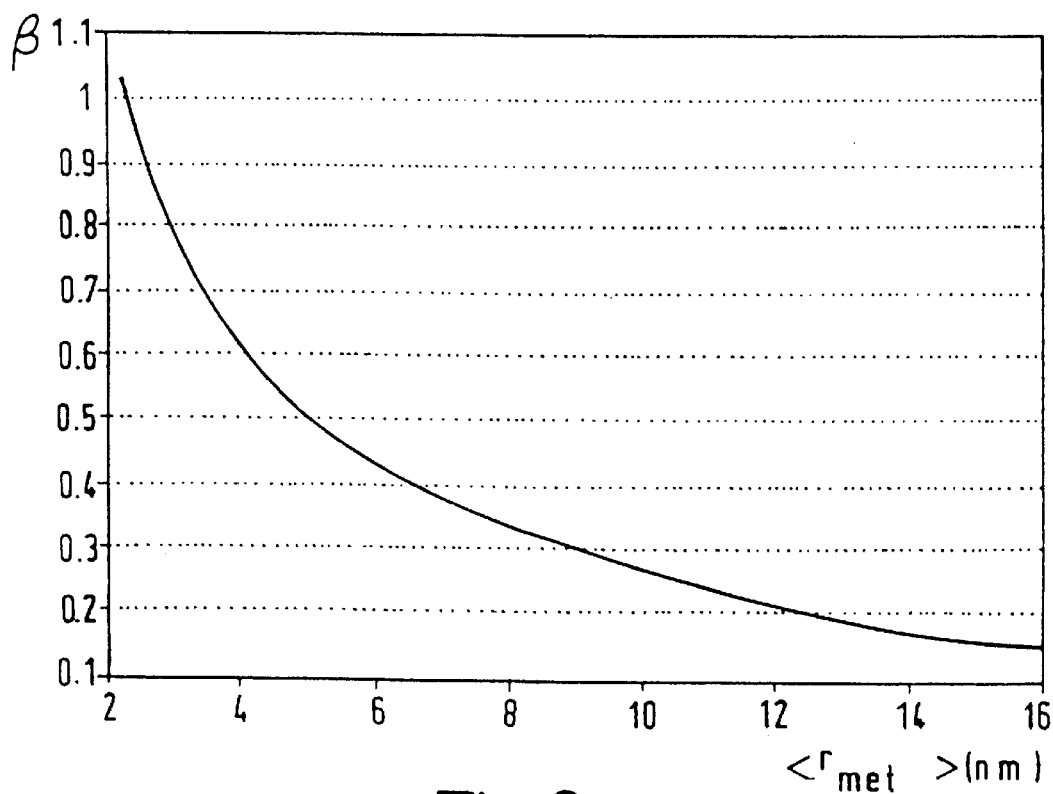
FIG. 6 is similar to FIG. 5, but with the response expressed in terms of a response exponent.

In FIG. 6, the response exponent β is plotted against apparent average crystallite size $<r_{met}>$, and shows that β increases systematically as $<r_{met}>$ decreases. This effect is significant, since a larger response exponent leads to better discrimination of carbon monoxide concentrations when the concentration is higher, in this case for concentrations lying between the recommended 8-hour exposure limit (50 ppm) and the 10 minute exposure limit (400 ppm).

Figure 7:
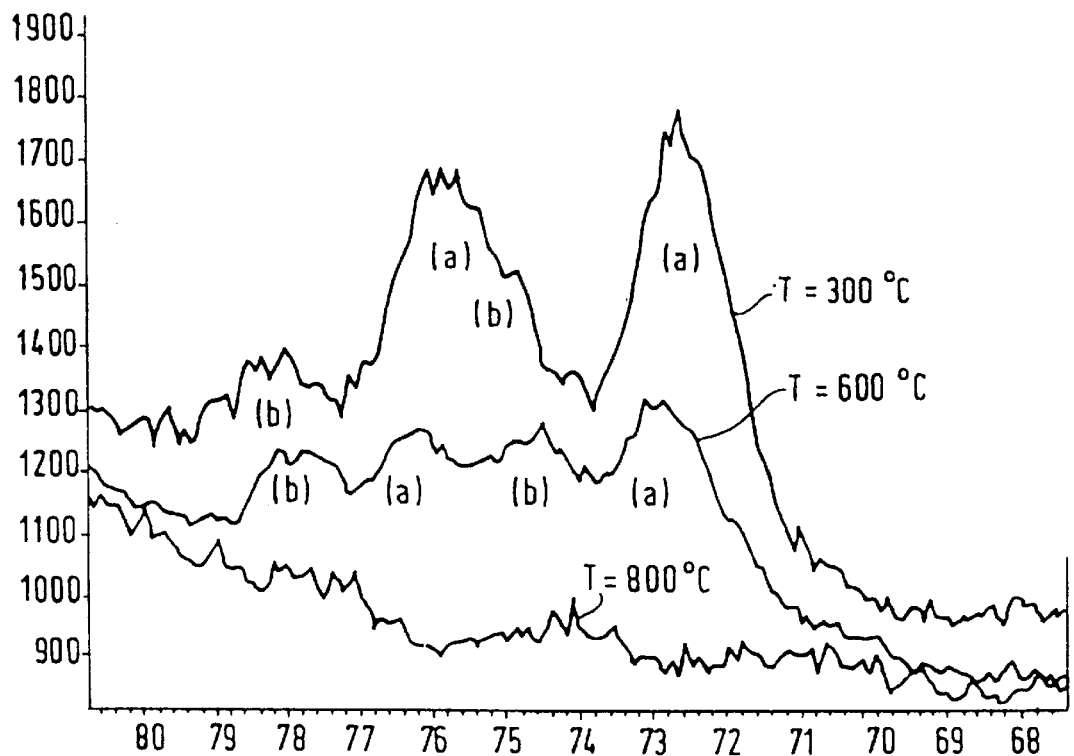
FIG. 7 shows part of three X-ray photoelectron spectrograms over a range of binding energy, for sensor materials which have been treated in different ways.
Figure 8:
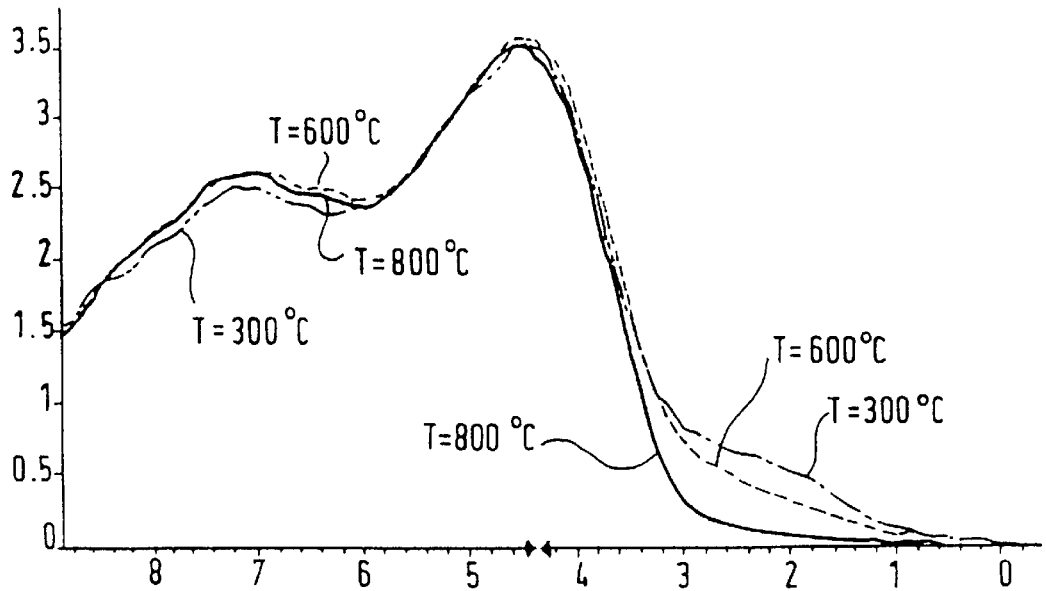
FIG. 8 shows another part of the same spectrograms, over another range of binding energy.

Reference is now made to FIGS. 7 and 8, which show X-ray photoelectron spectrograms for materials having nominally the same surface loading, but treated at the different decomposition temperatures T indicated, in order to give different average crystallite sizes. In FIGS. 7 and 8, the ordinate represents spectrum intensity (in counts per second in FIG. 7, and expressed as a percentage in FIG. 8); while the abscissa represents binding energy in electron-volts. It will be noted that in FIG. 8 the readings are taken over a range of much lower binding energy values than in FIG. 7.

The spectra taken in the region of the Pt core levels show, at the lowest decomposition temperature, signals attributable to platinum hydroxide species. These are labelled (a) in FIG. 7. As the decomposition temperature is increased, signals characteristic of platinum oxides appear. These are labelled (b) in FIG. 7. With further increase of decomposition temperature, the signals then become blurred; they decrease until, at the highest temperature, the signals have virtually vanished. Similar effects are seen at the valence band edge, where, as is seen in FIG. 8, the spectra show, for specimens treated at the lower decompositions temperatures, states associated with platinum at energy just above the tin dioxide valence band edge. With increasing decomposition temperature, these signals decline towards zero. The changes correlate with the marked diminution of platinum surface area with increasing decomposition temperature, and with the corresponding loss in sensitivity to carbon monoxide.

Example 2
Effect of the conductivity of tin dioxide

Tin dioxide of a pure, commercial grade was pressed into pellets as in Example 1. The pellets had a primary crystallite size of approximately 0.7 micrometer, not noticeably agglomerated (i.e. with an agglomerate size approximately equal to the primary crystallite size). The electrical resistance of these pellets was much higher than that of pellets prepared from calcined metastannic acid. Since the electrical resistivity of tin dioxide can be profoundly altered by small concentrations of adventitious impurities, this difference is to be expected.

Antimony-doped material was prepared by mixing together the required weights of tin dioxide and antimony pentoxide, in suspension in acetone. This was followed by drying, firing at 1000° C. for 12 hr, then grinding and pressing into pellets. The pellets so prepared had a mean primary crystallite size of approximately 0.5 micrometer and an apparent agglomerate size of 0.4 to 0.8 micrometer.

Some of the pellets were decorated with platinum as in Example 1. In this connection it should be noted that the high firing temperature is applied, to give a doped pellet, before any precious metal is applied, and does not adversely affect the ambient-temperature sensitivity of the resulting sensor.

X-ray photo-electron spectroscopy showed that the antimony in the specimens was actually segregated, the concentration at the surface being much higher than the average concentration calculated from the doping level. The gas sensitivity of antimony-doped pellets is therefore expected to depend on the details of the preparation of the doped pellets, insomuch as this changes the segregation of antimony. However both the response and the response time were found to vary systematically with the electrical conductivity of the undecorated pellets. The results obtained for pellets prepared from metastannic acid in Example 1 was consistent with the same trend.

Figure 9:
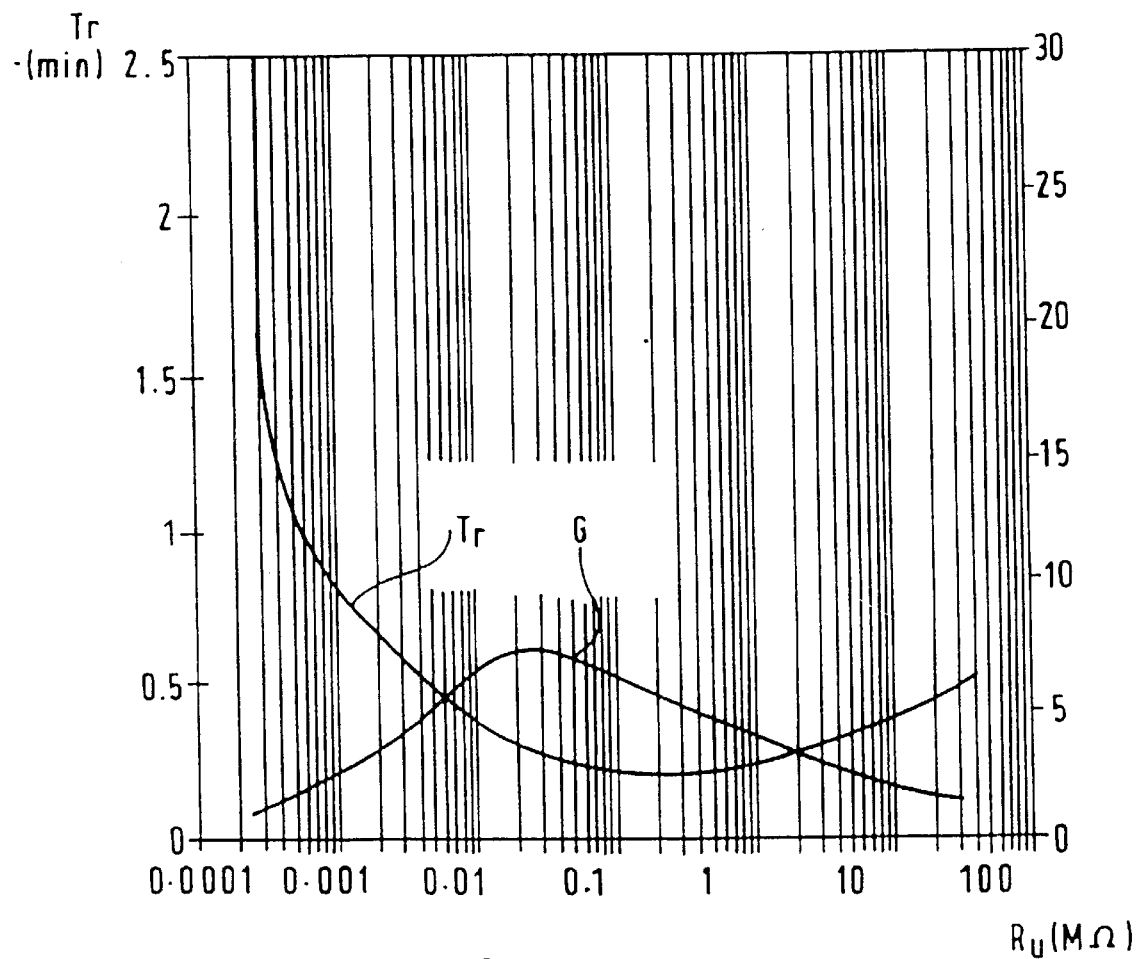
FIG. 9 is a diagram showing how the response time and sensitivity of tin dioxide pellets decorated with platinum, in an embodiment of the invention, vary with the electrical resistance of undecorated pellets.

In this connection, reference is now made to FIG. 9, in which the abscissa, on a logarithmic scale, represents the resistance $R_u$, of the undecorated pellets. The ordinate represents the time $T_r$ of response to a concentration of 20 ppm CO, and the response G at a CO concentration of 500 ppm CO, both responses being obtained at ambient temperatures.

The two curves show, respectively, the variation in $T_r$ and G with the resistance $R_U$, for a given loading of platinum. There was a broad optimum in performance, in respect of both response time and sensitivity, for pellets with electrical resistance, before decoration with platinum, in the range 5 kohm to 5 Mohm (resistivity in the range $3 \times 10^4$ to $3 \times 10^7$ ohm-cm).

Example 3
Sensors prepared by screen printing

Metastannic acid of a pure, commercial grade was mixed with antimonic oxide (0.25 wt %) and calcined at 1000° C. for 8 hours, to form an antimony-doped tin dioxide powder of small primary crystallite size. This powder was ground to a smooth paste with a solution of a platinum complex to give a final Pt content of 0.08 wt %. The powder was then dried, and the dried powder was mixed with a commercial screen printing vehicle to give a thick fluid intermediate material in the form of a polymer solution. This fluid was then screen-printed in a layer approximately 50 micrometers thick, over gold electrodes on an alumina substrate. The resulting printed sensors were dried, and then fired for 1 hour at 600° C. in a mildly reducing atmosphere. This caused the platinum complex to be decomposed so as to deposit highly active, fine-particle dispersion of Pt over the tin dioxide pore surface.

The screen-printing vehicle may typically be a solution of cellulose acetate in terpiniol.

Example 4
Use of an enclosed housing

Figure 10:
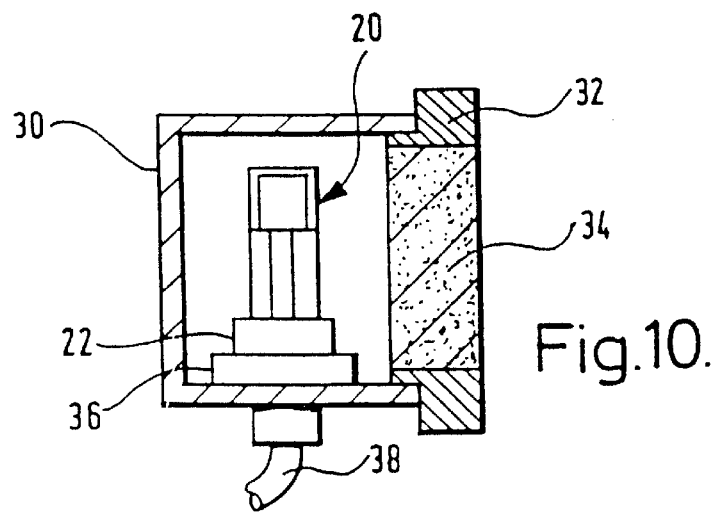
FIG. 10 is a diagrammatic cross sectional view of one form of mounting for a sensor according to this invention.

FIG. 10 shows one practical embodiment of a mounting for the sensor, 20, comprising a housing 30, open at one side 32 and carrying a header 22 in which the sensor is removably fitted. The open side 32 is closed by a removable cap 32, which incorporates s sintered plug 34, of any suitable metal that is chemically inert to the target gas.

An encapsulated electrical circuit 36 (which may for example be as will be described below with reference to FIG. 13) may conveniently be mounted within the housing 30, from which electrical connections are taken via a cable 38 containing all necessary power and signal leads.

The atmosphere containing the target gas (CO) is able to pass freely through the plug 34 so as to reach the sensor. A previous screen or filter, for example, a graphite cloth filter or a previous plug, such as the plug 34 in figure 10 (but taking any convenient form) serves to protect the sensor from hostile matter in the environment. Where for example the sensor is arranged to detect carbon monoxide emitted by a domestic gas boiler, it may need to be protected from contact with substances that would degrade or poison the response, for example silicones, and which may be in the form of sprays. Some examples of detrimental substances are insecticides or furniture polish, or liquids such as water, or food particles or grease.

Signal Measurement

Figure 11:
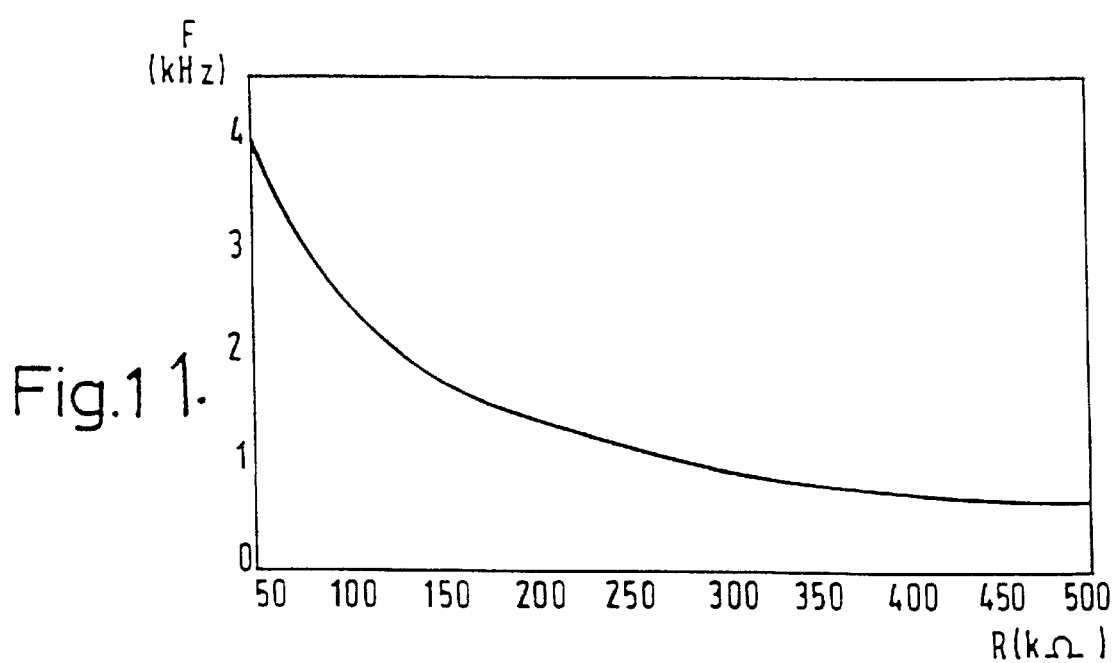
FIG. 11 is a circuit diagram for AC measurement of the response of the sensor according to the invention.

Reference is now made to FIG. 11, which shows one example of a simple measuring circuit 10 suitable for use in the AC measurement of the gas concentration represented by the resistance signals from the sensor in accordance with the invention. The circuit 10 comprises an oscillator 12 having a feedback loop 14, in which a header 16 is connected. The signal electrodes 18 of the sensor, which is indicated diagrammatically at 20, are connected to the header 16, so that the sensor itself constitutes one of the two working elements of the resistive-capacitive feedback network that controls the oscillator frequency. This frequency is inversely proportional to the sensor resistance.

The resistance signals from the sensor 20 thus vary the frequency of the output from the oscillator, to give a frequency output signal which represents the target gas concentration. This signal is taken, from pin 3 of an output header 22, to any suitable means (not shown) for processing and making use of the signal. For example, the frequency of the output signal can be measured by a digital counter circuit, and may be processed through a frequency-to-voltage converter. The said means may for example include a device for giving an alarm if the CO concentration exceeds a predetermined safe limit, and/or means for indicating, continuously or otherwise, the magnitude of the CO concentration. In a typical example, pin 1 of the output header 22 is at +12V, and pin 2 is at 0V.

Figure 12:
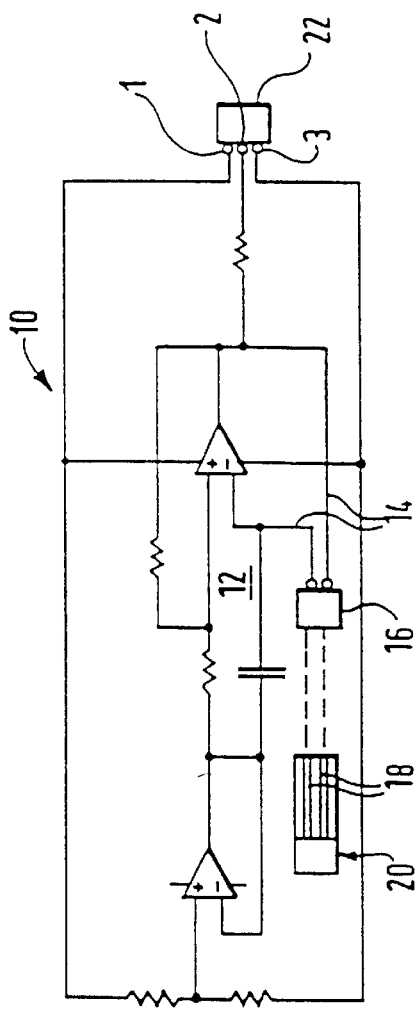
FIG. 12 shows the variation of oscillator frequency with sensor resistance in the circuit of FIG. 11.

In FIG. 12, the output signal frequency F at pin 3 of the header 22 is plotted against the resistance R of the sensor 20. The processing means interprets the frequency output signal accordingly, to give the CO concentration represented by the sensor resistance.

Other Features

The invention, as described thus far, provides CO sensors capable of operating at ambient temperatures, i.e. without the conventional use of applied heating in order to give an elevated operating temperature. It is however to be understood that the use of some applied heating is possible within the scope of the invention.

In particular, the sensor may be heated continously or intermittently during operation, in order to hold it at a constant operating temperature slightly above ambient. This is in order to avoid any possible effects of variation in the prevailing ambient temperature on the sensor resistance, and thus to reduce the likelihood of false alarms. The operating temperature should however be kept as low as possible above the ambient temperature, so as to minimise power consumption.

For example, a sensor likely to operate in a range of ambient temperatures between 0° C. and 80° C. may be heated to an operating temperature of 80°–85° C..

The sensor may, alternatively or in addition, be heated momentarily to a temperature above its operating temperature, in order to remove any water that may have condensed from the atmosphere in the pores of the sensor body. Such water tends to degrade the response. This momentary heating may be applied before measurement takes place, and/or at intervals during measurement, thus assisting the sensor to operate satisfactorily in wet atmospheres.

Power consumption is minimised by the use of momentary, rather than continuous, heating for this purpose. "Momentary heating" in this context means heating to a temperature high enough to vaporise the condensed moisture for a period of time only long enough to allow this vapour to dissipate. Typically such heating will give a temperature in the range 60°–120° C.

Figure 13:
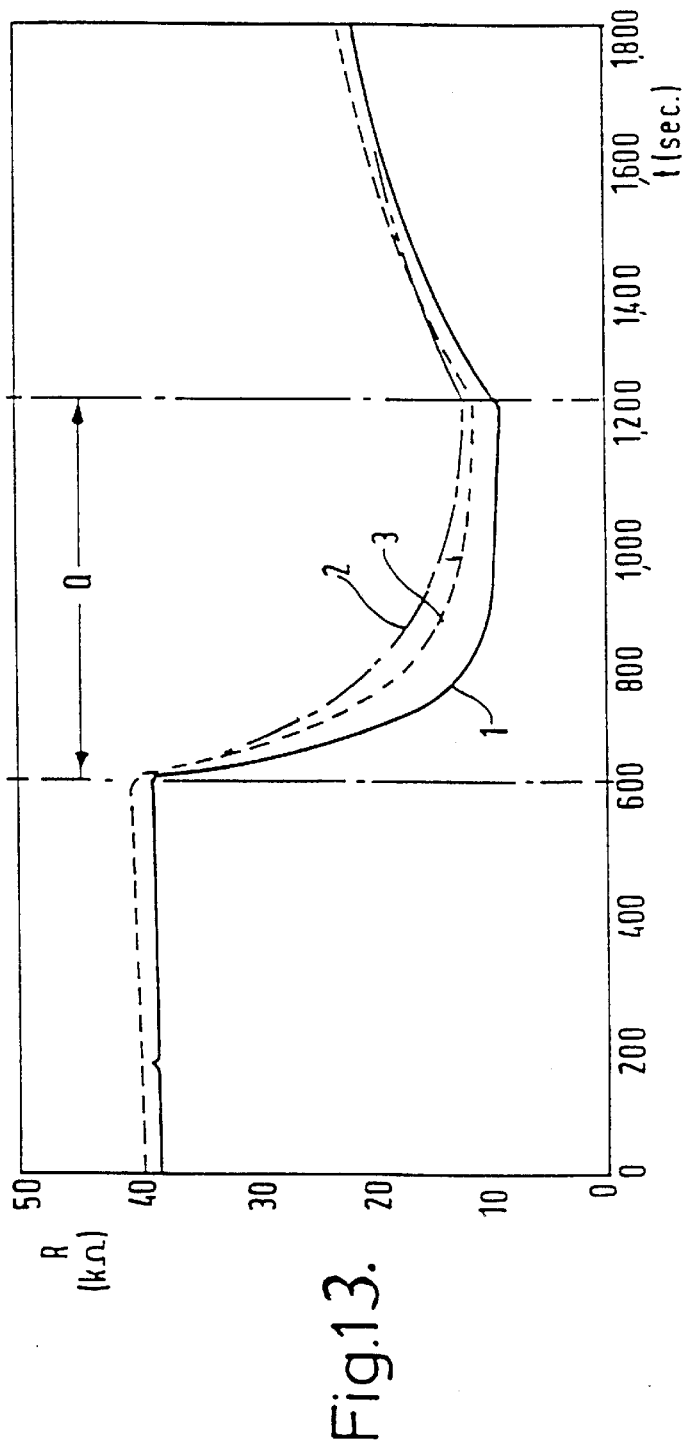
FIG. 13 is a graph showing the effect of moderate applied heating on the resistance response of an ambient-temperature sensor.

Reference is now made to FIG. 13, in which sensor resistance R is plotted against time t, with the sensor operating in wet air containing no carbon monoxide, except over the period indicated at Q, in which the air contains, in this example, CO at 400 ppm. FIG. 13 is the result of a test in which R was measured for a newly-prepared sensor (trace 1), and then again two weeks later (traces 2 and 3). The response had degraded to that shown in trace 2 during the two-week period, but brief heating to 75° C. improved the response to that shown in trace 3.

FIG. 13 illustrates how modest momentary heating, for example at regular predetermined intervals, may be used in order to ensure that a satisfactory response is maintained. This momentary heating can be controlled automatically, using any suitable known technique, for example by a time clock.

Where the sensor is made using screen printing to apply the electrodes on a substrate, the necessary heating element can easily be also applied by screen printing.

If desired, the surface of the completed sensor can be rendered hydrophobic by first drying the sensor at a temperature in excess of 100° C., and then treating the surface with a solution of chlorotrimethylsilane in hexane. Alternatively, the condensation of water vapour within the structure can be prevented by mixing, in the oxide sensor material, a hydrophobic ceramic material such as silicalite (which is a type of molecular sieve free of alkali metals and aluminium), to form a composite which can be fired on to a suitable substrate, yet having its surface substantially hydrophobic.

It is thought that the sensors described herein show a change of resistance in the presence of carbon monoxide as a consequence of carbon monoxide adsorbing on to the surface of the precious metal particles, so displacing oxygen. If the particles are small enough, then the result is a change in the Fermi level of electrons in the particle. As a consequence of this, there is a change in the Fermi level of electrons in the semiconductor, resulting in a change in the conductivity.

This mechanism can be generalised so that the sensor may be considered to consist of a variety of combinations of phases, in which one phase, in the form of small particles, acts as a detector of a gaseous species as a consequence of adsorption of a gas on to the surface of the particles. This detector phase decorates the surface of a second phase, which is chosen such that there is a contact potential developed between the two phases. This contact potential controls the electrical conductivity of the second phase, also referred to as a transducer phase. If the Fermi level of the detector phase particles changes upon gas adsorption, then the effect can be detected by a change in the conductivity of the transducer phase.

Small particles of a catalytic material also can cause combustion of the target gas (carbon monoxide for example). This combustion can serve to raise the temperature of the composite; and indeed, an increase in the temperature to some value significantly above room temperature is feasible. A second class of composite sensor can therefore be conceived, in which catalysed combustion of the target gas, whilst not giving a temperature rise large enough to cause a major effect on the conductivity, gives an effect sufficient to increase the speed of response of a sensor of the type described herein, or sufficient to drive condensed water off the surface of the sensor. Such a sensor may comprise: a first phase (transducer phase) of tin dioxide; a second phase (detector phase) consisting of small particles of platinum dispersed over the surface; and an optional third phase comprising an additional combustion catalyst, such as a Pt—Ir alloy dispersed on a suitable hydrophobic support, for example as described above.

A sensor of the type described herein, and incorporating a room-temperature combustion catalyst, can be configured as a self-diagnostic device. The reason is that the room-temperature catalyst imposes, within the porous sensor body, a concentration gradient of the gas to be detected. The sensing composite detects the local concentration of the gas within the porous body. With its electrodes positioned appropriately, the sensor will then reveal this concentration gradient by measurement of the signal derived from physically spaced parts of the sensor. Any failure of the sensing means or the catalyst can then be detected by a change in the relative values of the signals obtained from the physically spaced parts of the sensor.

TABLE 1

(see FIG. 3)

| N | $S_i$ (%) | T(°C.) | N | $S_i$ (%) | T(°C.) |
|---|---|---|---|---|---|
| 1 | 6.25 | 800 | 18 | 0.025 | 600 |
| 2 | 0.5 | 800 | 19 | 10 | 500 |
| 3 | 0.05 | 800 | 20 | 6.26 | 500 |
| 4 | 10 | 700 | 21 | 3.125 | 500 |
| 5 | 6.25 | 700 | 22 | 1.25 | 500 |
| 6 | 3.125 | 700 | 23 | 0.5 | 500 |
| 7 | 1.25 | 700 | 24 | 0.125 | 500 |
| 8 | 0.125 | 700 | 25 | 0.05 | 500 |
| 9 | 0.05 | 700 | 26 | 0.025 | 500 |
| 10 | 0.025 | 700 | 27 | 6.25 | 400 |
| 11 | 10 | 600 | 28 | 0.5 | 400 |
| 12 | 6.25 | 600 | 29 | 0.05 | 400 |
| 13 | 3.125 | 600 | 30 | 6.25 | 300 |
| 14 | 1.25 | 600 | 31 | 0.5 | 300 |
| 15 | 0.5 | 600 | 32 | 0.05 | 300 |
| 16 | 0.125 | 600 | | | |
| 17 | 0.05 | 600 | | | |

TABLE 2

(see FIG. 4)

| N | $S_i$ (%) | T(°C.) | N | $S_i$ (%) | T(°C.) |
|---|---|---|---|---|---|
| 1 | 6.25 | 800 | 18 | 0.025 | 600 |
| 2 | 0.5 | 800 | 19 | 10 | 500 |
| 3 | 0.05 | 800 | 20 | 6.25 | 500 |
| 4 | 10 | 700 | 21 | 3.125 | 500 |
| 5 | 6.25 | 700 | 22 | 1.25 | 500 |
| 6 | 3.125 | 700 | 23 | 0.5 | 500 |
| 7 | 1.25 | 700 | 24 | 0.125 | 500 |
| 8 | 0.125 | 700 | 25 | 0.05 | 500 |
| 9 | 0.05 | 700 | 26 | 0.025 | 500 |
| 10 | 0.025 | 700 | 27 | 6.25 | 400 |
| 11 | 10 | 600 | 28 | 0.5 | 400 |
| 12 | 6.25 | 600 | 29 | 0.05 | 400 |
| 13 | 3.125 | 600 | 30 | 6.25 | 300 |
| 14 | 1.25 | 600 | 31 | 0.5 | 300 |
| 15 | 0.5 | 600 | 32 | 0.05 | 300 |
| 16 | 0.125 | 600 | | | |
| 17 | 0.05 | 600 | | | |

We claim:

1. A resistive gas sensor comprising a porous sensor body of a semiconducting oxide, a metallic phase decorating pore surfaces of said sensor body, said porous sensor body being formed of primary crystallites agglomerated together so as to exhibit a primary crystallite size and an agglomerate size, said agglomerate size being less than 10 times said primary crystallite size, said primary crystallite size having an average diameter of less than 5 micrometer, from 0.05 to 80% of said pore surfaces being covered by said metallic phase, said metallic phase consisting of particles having an average size of less than 50 nanometers wherein the sensor detects the concentration of a target gas in an atmosphere at a temperature of 110° C. or less.

2. A sensor according to claim 1, wherein said oxide is tin dioxide having a conductivity no greater than $2 \times 10^{-4}$ Siemen/cm.

3. A sensor according to claim 1, wherein from 1–30% of said pore surfaces are covered by said metallic phase.

4. A sensor according to claim 1, comprising a substrate carrying the said sensor body, wherein said substrate is substantially hydrophobic.

5. A sensor according to claim 1, wherein the said semiconducting oxide contains a dopant material.

6. A sensor according to claim 1, and further including a room-temperature combustion catalyst on said pore surfaces of said semiconducting oxide.

7. Apparatus for detecting or measuring the concentration of a target gas in an atmosphere at a temperature of 100° C. or less, comprising an oscillator and a resistive-capacitive feedback network, said feedback network including a sensor according to claim 1 connected to said oscillator for varying the oscillator frequency in response to changes in the resistance of said sensor, so that said apparatus can produce output signals, said output signals representing target gas concentrations in the form of frequency signals.

8. A sensor according to claim 1, wherein the said pore surfaces of said sensor body are substantially hydrophobic.

9. A sensor according to claim 8, wherein said sensor body comprises the said semiconducting oxide mixed with a hydrophobic ceramic material.

10. A sensor according to claim 8, wherein said pore surfaces are surface-treated with a hydrophobic material.

11. A method of making a resistive gas sensor, comprising the steps of forming a porous sensor body wherein said porous sensor body is formed of primary crystallite agglomerated together so as to exhibit a primary crystallite size and an agglomerate size, said method further including the steps of making an intermediate material comprising a semiconducting oxide containing at least one metallic compound, decomposing said metallic compound so as to deposit a metallic phase decorating pore surfaces of said sensor body, said metallic phase covering from 0.05 to 80% of said pore surfaces and consisting of particles having an average size of less than 50 nanometers, said agglomerate size being less than 10 times the size of said primary crystallite, said primary crystallite size having an average diameter of less than 5 micrometers and wherein a method of detecting the concentration of a target gas in an atmosphere at a temperature of 110° C. or less, including the steps of bringing the atmosphere and a resistive gas sensor into contact with each other, and measuring changes in the electrical resistance of the sensor.

12. A method according to claim 11 wherein, in step (1), the range of pore sizes is controlled so as to be such as to minimise capillary condensation of atmospheric water vapour into the pores.

13. A method according to claim 11, wherein the sensor operates at the prevailing ambient temperature, application of heat to the sensor being absent.

14. A method according to claim 11, wherein heat is applied to the sensor to raise its temperature of operation to a constant value just high enough to eliminate any effects of variation in ambient temperature on the sensor resistance.

15. A method according to claim 11, including the step of applying momentary heating to the sensor once or intermittently, to a temperature and for a period of just sufficient magnitude to allow any condensed moisture present at the sensor to dissipate, the sensor being at the prevailing ambient temperature for the major part of its operation.

16. A method as claimed in claim 11, wherein said step of making an intermediate material comprises the step of making a mixture containing said semiconducting oxide and a metal compound, and further including the step of printing said mixture onto a substrate.

17. A method as claimed in claim 11, and further including the step of controlling the pore size during the said step of forming a porous sensor body so as to minimise capillary condensation of atmospheric water vapour into the pores.

18. A method as claimed in claim 11, wherein said step of making a mixture containing said semiconducting oxide further includes the step of adding a room-temperature combustion catalyst in said mixture.

19. A method as claimed in claim 11, wherein said step of making a mixture containing said semiconducting oxide further includes the steps of mixing a hydrophobic ceramic material with said semiconducting oxide to form a composite, firing said composite onto a substantially hydrophobic surface of a support element, and dispersing a room-temperature combustion catalyst on said substantially hydrophobic surface so that the sensor body comprises a three-phase composite.

* * * * *